US007026141B2

(12) United States Patent
Shuman

(10) Patent No.: US 7,026,141 B2
(45) Date of Patent: Apr. 11, 2006

(54) TOPOISOMERASE-BASED REAGENTS AND METHODS FOR MOLECULAR CLONING

(75) Inventor: Stewart Shuman, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 15 days.

(21) Appl. No.: 10/360,478

(22) Filed: Feb. 7, 2003

(65) Prior Publication Data

US 2003/0215925 A1   Nov. 20, 2003

Related U.S. Application Data

(60) Continuation of application No. 08/898,517, filed on Jul. 22, 1997, now Pat. No. 6,548,277, which is a division of application No. 08/358,344, filed on Dec. 19, 1994, now Pat. No. 5,766,891.

(51) Int. Cl.
  *C12P 19/34* (2006.01)
  *C07H 21/04* (2006.01)
  *C12N 15/11* (2006.01)

(52) U.S. Cl. .................... 435/91.4; 435/91.1; 536/23.1

(58) Field of Classification Search ............... 435/91.5, 435/91.1, 91.4
See application file for complete search history.

(56) References Cited

U.S. PATENT DOCUMENTS

| 4,661,450 | A  | 4/1987 | Kempe et al. ............ 435/172.3 |
| 4,800,159 | A  | 1/1989 | Mullis et al. ............ 435/172.3 |
| 5,624,826 | A  | 4/1997 | Kato et al. ................. 435/91.4 |
| 5,766,891 | A  | 6/1998 | Shuman et al. .......... 435/91.41 |
| 6,238,884 | B1 | 5/2001 | Short et al. ................ 435/69.1 |
| 6,280,977 | B1 | 8/2001 | Liang et al. ............... 435/91.2 |
| 6,291,213 | B1 | 9/2001 | Rothstein ................... 435/91.2 |
| 6,548,277 | B1 | 4/2003 | Shuman et al. ............ 435/91.4 |

FOREIGN PATENT DOCUMENTS

| EP | 0373914   | 7/1994  |
| EP | 0625572   | 4/2001  |
| WO | WO8504898 | 11/1985 |
| WO | WO9429443 | 12/1994 |
| WO | WO9619497 | 6/1996  |
| WO | WO9634981 | 11/1996 |
| WO | WO9724455 | 7/1997  |
| WO | WO9820122 | 5/1998  |
| WO | WO9855502 | 12/1998 |
| WO | WO9856943 | 12/1998 |
| WO | WO0012687 | 3/2000  |
| WO | WO0056878 | 9/2000  |
| WO | WO0162943 | 8/2001  |
| WO | WO0262892 | 8/2001  |
| WO | WO0216594 | 2/2002  |

OTHER PUBLICATIONS

Carninci et al. "High efficiency selection of full-length cDNA by improved biotinylated cap trapper," DNA Research 4:61-66 (1997).

Carninci et al. "High-efficiency full-length cDNA cloning by biotinylated CAP trapper," Genomics 37(3):327-36(1996).

Cheng and Shuman, "Recombinogenic flap ligation pathway for intrinsic repair of topoisomerase IB-induced double-strand breaks," Mol. Cell. Biol. 20(21):8059-8068 (2000).

Cheng and Shuman, "Site-specific DNA transestification by vaccinia topoisomerase: Role of specific phosphates and nucleosides," Biochemistry 38(50):16599-612 (1999).

Cheng et al. "Conservation of structure and mechanism between eukaryotic topoisomerase I and site-specific recombinases," Cell 92(6):841-50 (1998).

Cheng et al. "Mutational analysis of 39 residues of vaccinia DNA topoisomerase identifies Lys-220, Arg-223, and Asn-228 as important for covalent catalysis," J. Biol. Chem. 272(13):8263-9 (1997).

DiGate and Marians, "Molecular cloning and DNA sequence analysis of *Escherichia coli* topoB, the gene encoding topoisomerase III," J. Biol. Chem. 264(30);17924-17930 (1989).

Edery et al. "An efficient strategy to isolate full-length cDNAs based on an mRNA cap retention procedure (CAPture)," Mol. Cell. Biol. 15(6):3363-3371 (1995).

Ericsson et al. "Characterization of ts16, a temperature-sensitive mutant of vaccinia virus," J. Virol. 69(11):7072-86 (1995).

Gross and Shuman, "Vaccinia virions lacking the RNA helicase nucleoside triphosphate phosphohydrolase II are defective in early transcription," J. Virol. 70(12):8549-5 (1996).

Haghighat and Sonenberg, "eIF4G dramatically enhances the binding of eIF4E to the mRNA 5'- cap structure," J. Biol. Chem. 272(35):21677-21680 (1997).

Haghighat et al. "The eIF4G-eIF4E complex is the target for direct cleavage by the rhinovirus 2A proteinase," J. Virol. 70:8444-8450 (1996).

(Continued)

Primary Examiner—Nancy Vogel
(74) Attorney, Agent, or Firm—John P. White, Esq.; Cooper & Dunham LLP

(57) ABSTRACT

This invention provides a modified vaccinia topoisomerase enzyme containing an affinity tag which is capable of facilitating purification of protein-DNA complexes away from unbound DNA. This invention further provides a modified sequence specific topoisomerase enzyme.

This invention provides a method of ligating duplex DNAs, a method of molecular cloning of DNA, a method of synthesizing polynucleotides, and a method of gene targeting.

Lastly, this invention provides a recombinant DNA molecule composed of segments of DNA which have been joined ex vivo by the use of a sequence specific topoisomerase and which has the capacity to transform a suitable host cell comprising a DNA sequence encoding polypeptide activity.

23 Claims, 12 Drawing Sheets

OTHER PUBLICATIONS

Henningfeld and Hecht, "A model for topoisomerase I-mediated insertions and deletions with duplex DNA substrates containing branches, nicks, gaps," Biochemistry 34(18): 6120-9 (1995).
Invitrogen Corporation, Carlsbad, California, catalog pages 18, 29, 43, 44, 49-52 (1998).
Kane and Shuman, "Vaccinia virus morphogenesis is blocked by a temperature-sensitive mutation in the 17 gene that encodes a virion component," J. Virol. 67(5):2689-98 (1993).
Kato et al. "Construction of a human full-length cDNA bank," Gene 150:243-250 (1994).
Klemm et al. "Peptide inhibitors of DNA cleavage by tyrosine recombinases and topoisomerases," J. Mol. Biol. 299(5):1203-16 (2000).
Klemperer et al. "Identification and characterization of the orf virus type I topoisomerase," Virology 206:203-215 (1995).
Krogh and Shuman, "Catalytic mechanism of DNA topoisomerase IB," Mol. Cell 5(6):1035-41 (2000).
Krogh and Shuman, "DNA strand transfer catalyzed by vaccinia topoisomerase: peroxidolysis and hydroxylaminolysis of the covalent protein-DNA intermediate," Biochemistry 39(21):6422-32 (2000).
Krogh and Shuman, "Vaccinia topoisomerase mutants illuminate conformational changes during closure of the protein clamp and assembly of a functional active site," J. Biol. Chem. (2001).
Krogh et al. "Effect of 2'-5' phosphodiesters on DNA transesterification by vaccinia topoisomerase," J. Biol. Chem. 276(24):20907-20912 (2001).
Krogh et al. "Melanoplus sanguinipes entomopoxvirus DNA topoisomerase: site-specific DNA transesterification and effects of 5'-bridging phosphorothiolates," Virology 264(2): 441-51 (1999).
Liu et al. "Mapping the 5' and 3' ends of tetrahymena thermophila mRNAs using ligase mediated amplification of cDNA ends (RLM-Race)," Nucleic Acids Res. 21(21):4954-4960 (1993).
Krogh and Shuman, "DNA strand transfer catalyzed by vaccinia topoisomerase: peroxidolysis and hydroxylaminolysis of the covalent protein-DNA intermediate," Biochemistry 39(21):6422-32 (2000).
Lockard et al. "Labeling of eukaryotic messenger RNA $5^2$ terminus with phosphorus-32: Use of tobacco acid pyrophosphatase for removal of cap structure," Gene Amp. Anal. 2:229-251 (1981).
Maruyama et al. "Oligo-Capping: A simple method to replace the cap structure fo eukaryotic mRNAs with oligonucleotides," Gene 138:171-174 (1994).
Matthews et al. "Analytical strategies for the use of DNA probes," Anal. Biochem. 169:1-25 (1988).
Morham and Shuman, "Covalent and noncovalent DNA binding by mutants of vaccinia DNA topoisomerase I," J. Biol. Chem. 267:15984-15992 (1992).
Morham and Shuman, "Phenotypic selection and characterization of mutant alleles of a eukaryotic DNA topoisomerase I," Genes. Dev. 4(4):515-24 (1990).
Palaniyar et al. "SFV topoisomerase: sequence specificity in a genetically mapped interval," Virology 221:351-354 (1996).
Petersen and Shuman, "DNA strand transfer reactions catalyzed by vaccinia topoisomerase: hydrolysis and glycerololysis of the covalent protein-DNA intermediate," Nucleic Acids Res. 25(11):2091-7 (1997).
Petersen and Shuman, "Histidine 265 is important for covalent catalysis by vaccinia topoisomerase and is conserved in all eukaryotic type I enzymes," J. Biol. Chem. 272(7):3891-6 (1997).
Petersen et al. "Characterization of a DNA topoisomerase encoded by Amsacta moore entomopoxvirus," Virology 230(2):197-206 (1997).
Petersen et al. "Mutations within a conserved region of vaccinia topoisomerase affect the DNA cleavage-religation equilibrium," J. Mol. Biol. 1263(2):181-95 (1996).
Salazar et al. "The DNA strand in DNA:RNA hybrid duplexes is neither B-form nor A-form in solution," Biochemistry 32(16);4207-15 (1993).
Sekiguchi and Shuman, "Covalent DNA binding by vaccinia topoisomerase results in unpairing of the thymine base 5' of the scissile bond," J. Biol. Chem. 271(32):19436-42 (1996).
Sekiguchi and Shuman, "Domain structure of vaccinia DNA ligase," Nucleic Acids Res. 25(4):727-43(1997).
Sekiguchi and Shuman, "Identification of contacts between topoisomerase I and its target DNA by site-specific photocrosslinking," EMBO J. 15(13):3448-57 (1996).
Sekiguchi and Shuman, "Mutational analysis of vaccinia virus topoisomerase identifies residues involved in DNA binding," Nucleic Acids Res. 25(18):3649-56 (1997).
Sekiguchi and Shuman, "Nick sensing by vaccinia virus DNA ligase requires a 5' phosphate at the nick and occupancy of the adenylate binding site on the enzyme," J. Virol. 71(12):9679-84 (1997).
Sekiguchi and Shuman, "Proteolytic footprinting of vaccinia topoisomerase bound to DNA," J. Biol. Chem. 270(19): 11636-45 (1995).
Sekiguchi and Shuman, "Requirements for noncovalent binding of vaccinia topoisomerase I to duplex DNA," Nucleic Acids Res. 22(24):5360-5 (1994).
Sekiguchi and Shuman, "Site-specific ribonuclease activity of eukaryotic DNA topoisomerase I," Mol. Cell 1(1):89-97. (1997).
Sekiguchi and Shuman, "Stimulation of vaccinia topoisomerase I by nucleoside triphosphates," J. Biol. Chem. 269(47):29760-4 (1994).
Sekiguchi and Shuman, "Vaccinia topoisomerase binds circumferentially to DNA," J. Biol. Chem. 269(50):31731-4 (1994).
Sekiguchi et al. "Kinetic anlysis of DNA and RNA strand transfer reactions catalyzed by vaccinia topoisomerase," J. Biol. Chem. 272(25):15721-15728 (1997).
Sekiguchi et al. "Mechanism of inhibition of vaccinia DNA topoisomerase by novobiocin and coumermycin," J. Biol Chem. 271(4):2313-22 (1996).
Sekiguchi et al. "Resolution of a Holliday junction by vaccinia topoisomerase requires a spacer DNA segment 3' of the CCCTT/ cleavage sites," Nucleic Acids Res. 28(14): 2658-63 (2000).
Sekiguchi et al. "Resolution of Holliday junctions by eukaryoric DNA topoisomerase I" Proc. Natl. Acad. Sci U.S.A. 93(2):785-9 (1996).
Shatkin, "Capping of eukaryotic mRNAs," Cell 9(4):645-653 (1976).
Shuman and Moss, "Identification of a vaccinia virus gene encoding a type I DNA topoisomerase," Proc. Natl. Acad. Sci. U.S.A. 84:7478-7482 (1987).

Shuman and Prescott, "Specific DNA cleavage and binding of vaccinia virus DNA topoisomerase I," J. Biol. Chem. 265:17826-17836 (1990).

Shuman and Turner, "Site-specific interaction of vaccinia virus topoisomerase I with base and sugar moieties in duplex DNA," J. Biol. CHem. 268(25):18943-50 (1993).

Shuman et al. "Characterization of vaccinia virus DNA topoisomerase I expressed in *Escherichia coli*," J. Biol. Chem. 263:16401-16407 (1988).

Shuman et al. "Insertional mutagenesis of the vaccinia virus gene encoding a type I DNA topoisomerase: evidence that the gene is essential of virus growth," Virology 170(1):302-6 (1989).

Shuman et al. "Intramolecular synapsis of duplex DNA by vaccinia topoisomerase," EMBO J. 16(21):6584-9 (1997).

Shuman et al. "Mapping the active-site tyrosine of vaccinia virus DNA topoisomerase I," Proc. Natl. Acad. Sci. U.S.A. 86(24):9793-7 (1989).

Shuman, "Analysis of topoisomerase-DNA interactions by electrophoretic mobility shift assay," Methods Mol. Biol. 95:65-74(2001).

Shuman, "DNA strand transfer reactions catalyzed by vaccinia topoisomerase I," J. Biol. Chem. 267:8620-8627 (1992).

Shuman, "Novel approach to molecular cloning and polynucleotide synthesis using vaccinia DNA topoisomerase," J. Biol. Chem. 269(51):32678-32684 (1994).

Shuman, "Polynucleotide ligase activity of eukaryotic topoisomerase I," Mol. Cell. 1(5):741-8 (1998).

Shuman, "Recombination mediated by vaccinia virus DNA topoisomerase I in *Escherichia coli* is sequence specific," Proc. Natl. Acad. Sci. U.S.A. 88(22):10104-8 (1991).

Shuman, "Site-specific DNA cleavage by vaccinia virus DNA topoisomerase I. Role of nucleotide sequence and DNA secondary structure," J. Biol. Chem. 266(3):1796-1803 (1991).

Shuman, "Site-specific interaction of vaccinia virus topoisomerase I with duplex DNA. Minimal DNA substrate for strand cleavage in vitro," J. Biol. Chem. 266(17):11372-11379 (1991).

Shuman, "Two classes of DNA end-joining reactions catalyzed by vaccinia topoisomerase I," J. Biol. Chem. 267:16755-16758 (1992).

Shuman, "Vaccinia DNA topoisomerase I promotes illegitimate recombination in *Escherichia coli*," Proc. Natl. Acad. Sci. U.S.A. 86(10):3489-93 (1989).

Shuman, "Vaccinia virus DNA ligase: specificity, fidelity, and inhibition," Biochemistry 34:16138-16147 (1995).

Shuman, "Vaccinia virus DNA topoisomerase: a model eukaryotic type IB enzyme," Biochim. Biophys. Acta. 1400 (1-3):321-37 (1998).

Stivers et al. "Stereochemical outcome and kinetic effects of Rp- and Sp-phosphorothioate substitutions at the cleavage site of vaccinia type I DNA topoisomerase," Biochemistry 39(18):5561-72 (2000).

Stivers et al. "Vaccinia DNA topoisomerase I: single-turnover and steady-state kinetic analysis of the DNA strand cleavage and ligation reactions," Biochemistry 33(1):327-39 (1994).

Theus, "A simple assay for determining the capping efficiencies of RNA polymerases used for in vitro transcription," Biotechniques 9(5):610-615 (1990).

Wang and Shuman, "Deletions at the carboxyl terminus of vaccinia DNA topoisomerase affect DNA binding and enhance distributivity in DNA relaxation," Biochemistry 36(13):3909-16 (1997).

Wang et al. "Mutational analysis of 26 residues of vaccinia DNA topoisomerase identifies Ser-204 as important for DNA binding and cleavage," Biochemistry 36(26):7944-50 (1997).

Wexler et al. "A procedure to amplify cDNA from dsRNA templates using the Polymerase chain reaction," Methods Mol. Cell. Biol. 2:273-279 (1991).

Wittschieben and Shuman, "Mechanism of DNA transesterification by vaccinia topoisomerase: catalytic contributions of essential residues Arg-130, Gly-132, Tyr-136 and Lys-167," Nucleic Acids Res. 25(15):3001-8 (1997).

Wittschieben and Shuman, "Mutational analysis of vaccinia DNA topoisomerase defines amino acid residues essential for covalent catalysis," J. Biol. Chem. 269(47):29978-83 (1994).

Wittschieben et al. "Replacement of the active site tyrosine of vaccinia DNA topoisomerase by glutamate, cysteine or histidine converts the enzyme into a site-specific endonuclease," Nucleic Acids Res. 26(2):490-6 (1998).

Woodfield et al. "Vaccinia topoisomerase and Cre recombinase catalyze direct ligation of activated DNA substrates containing a 3'-para-nitrophenyl phosphate ester," Nucleic Acid Res. 28(17):3323-31 (2000); and.

Yang et al. "A eukaryotic enzyme that can disjoin dead-end covalent complexes between DNA and type I topoisomerases," Proc. Natl. Acad. Sci. U.S.A. 93(21):11534-9 (1996).

Arnot et al., "DNA-RNA hybrid secondary structures" J. Mol. Biol. 188(4): 631-640 (1986).

Chong, S: et al., "Single column purification of free recombinant proteins using a self-cleavable affinity tag derived from a protein splicing element," Gene 192(2): 271-281 (1997).

Janknecht et al., "Rapid and efficient purification of native histidine-tagged protein expressed by recombinant vaccinia virus," Proc. Natl. Acad. Sci. U.S.A. 88:8972-8976 (1991).

Schmitt et al., "Affinity purification of histidine-tagged proteins," Mol. Biol. Reports 18:223-230 (1993).

Supplementary European Search Report issued on Nov. 30, 2004 in connection with related European Patent Application No. 95943753.4, on behalf of Sloan-Kettering Institute for Cancer Research, based on PCT International Application No. PCT/US95/16099, filed Dec. 12, 1995.

1. No acceptor
2. pUC-AccI/CIP
3. pUC-AccI
4. pUC-Eco/CIP
5. pUC-Sma/CIP
6. pUC-Hind/CIP

TTCGATATCATC                      CAGATCTCATAT
A           GCCCTTAGCT            T           GCCCTTAGCT
A           CGGGAATCGA*           T           CGGGAATCGA*
  GTCTAGAGTATA                      AAGCTATAGTAG
```

```
*AGCTAAGGGCATATGAGATCTGAATTCGATATCATCGCCCTTAGCT    S300
 TCGATTCCCGTATACTCTAGACTTAAGCTATAGTAGCGGGAATCGA*   S301
```

```
 AGCTAAGGGCATATGAGATCTGAATTCGATATCATCGCCCTTAGCT    S300
 TCGATTCCCGTATACTCTAGACTTAAGCTATAGTAGCGGGAATCGA
                     TA
                     TA
            S304     GC     S303
                     GC
                     TA
                     AT
                     CG
                     CG
                     AT
                     TA
                     GC
                     GC
                     TA
                     CG
                     GC
                     GC
                     GC
                     AT
                     AT
                     TA
                     CG
                     GC
                     AT
```

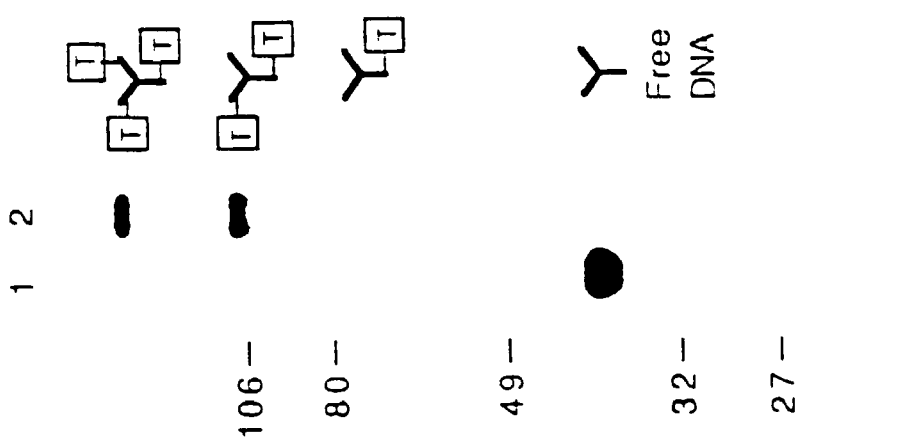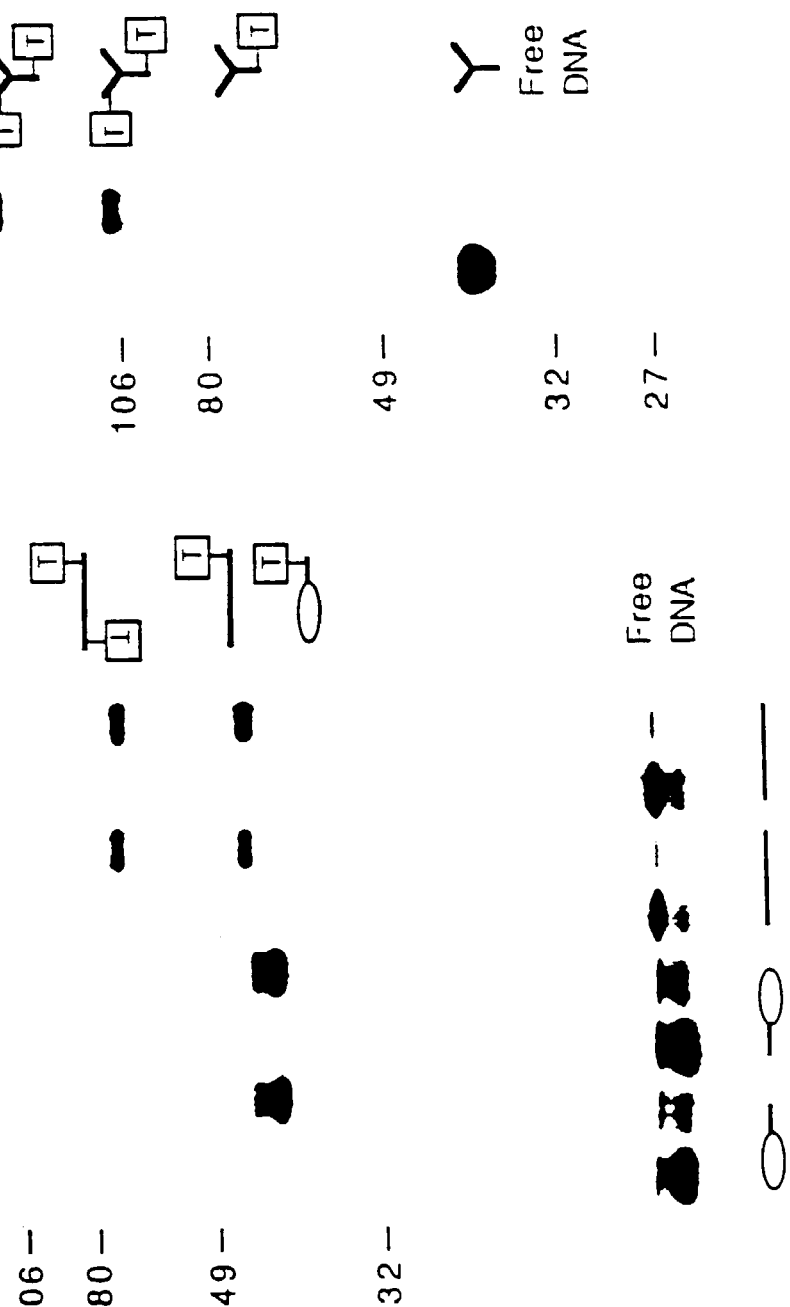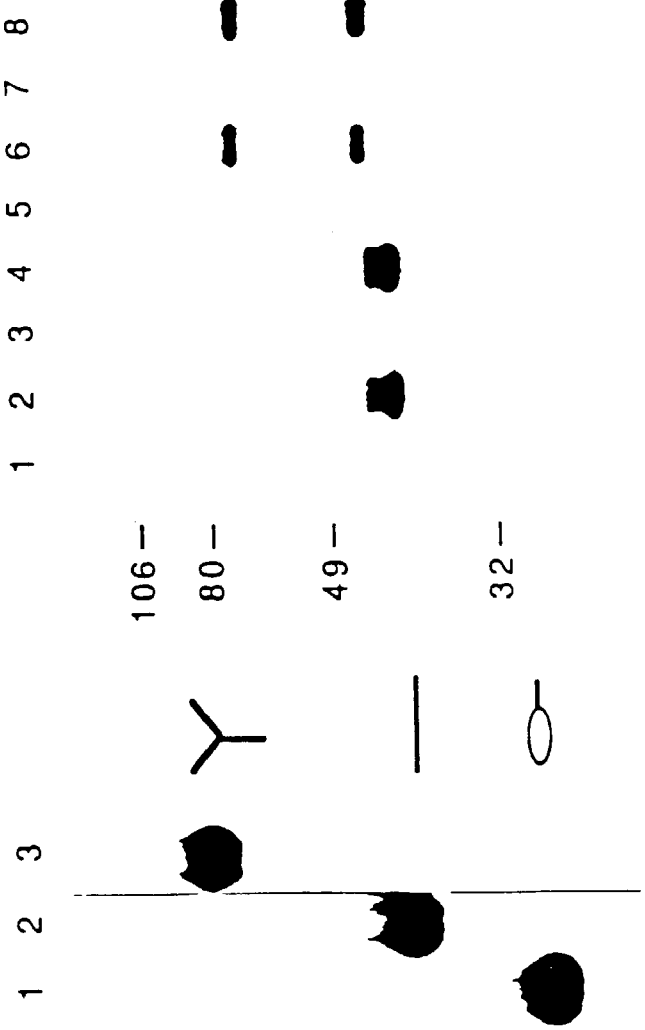

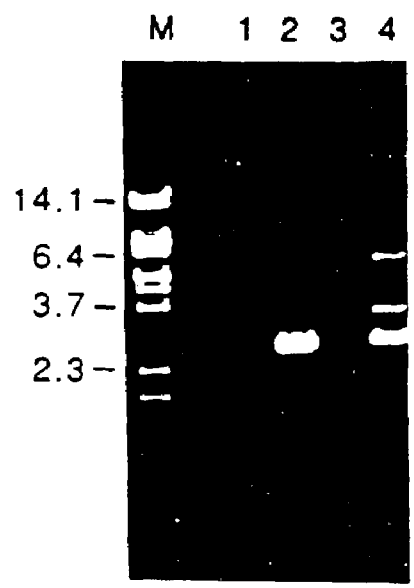
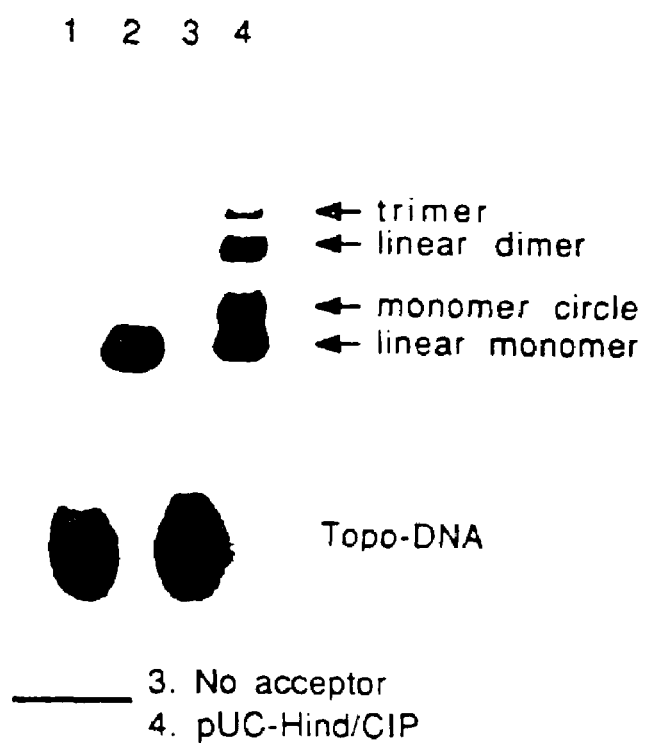
FIGURE 4A
FIGURE 4B
1. No acceptor
2. pUC-Hind/CIP
3. No acceptor
4. pUC-Hind/CIP pUC18 pUC-T11

FIGURE 5D

```
         NdeI   BglII           EcoRV
AGCTAAGGGCATATGAGATCTGAATTCGATATCATCGCCCTTAGCT
TCGATTCCCGTATACTCTAGACTTAAGCTATAGTAGCGGGAATCGA
```

DNA Linkers

○— 1. No acceptor
2. pUC-Hind/CIP
Y 3. No acceptor
4. pUC-Hind/CIP

Topo-DNA

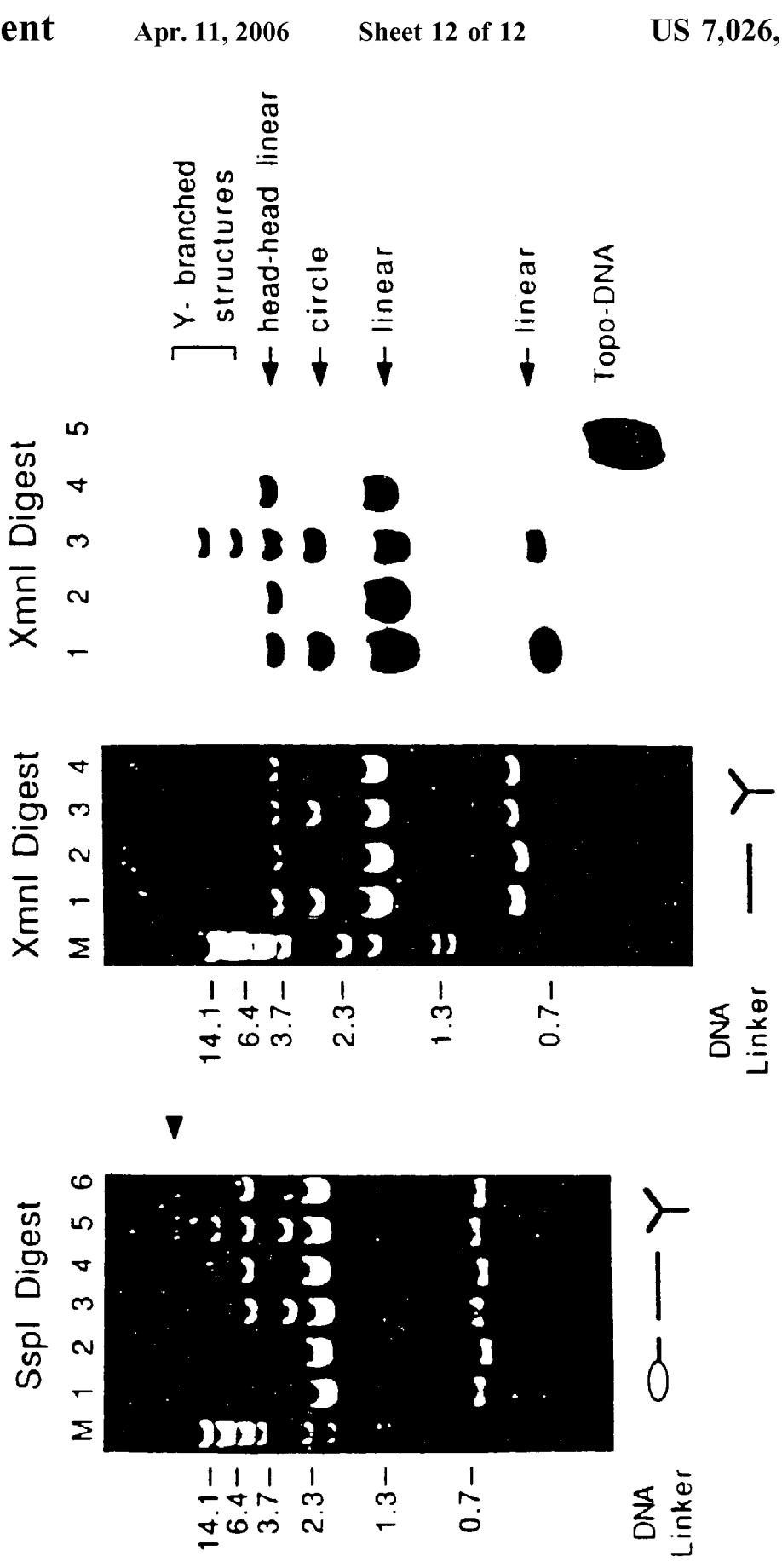

US 7,026,141 B2

TOPOISOMERASE-BASED REAGENTS AND METHODS FOR MOLECULAR CLONING

This application is a continuation of U.S. Ser. No. 08/898,517, filed Jul. 22, 1997, now U.S. Pat. No. 6,548,277, which is a divisional of U.S. Ser. No. 08/358,344, filed Dec. 19, 1994, now U.S. Pat. No. 5,766,891, the contents of which are hereby incorporated by reference.

This invention was made with support under Grant No. GM-46330 from the National Institutes of Health, U.S. Department of Health and Human Services. Accordingly, the United States Government has certain rights in the invention.

Throughout this application, various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THE INVENTION

Construction of chimaeric DNA molecules in vitro relies traditionally on two enzymatic steps catalyzed by separate protein components. Site-specific restriction endonucleases are used to generate linear DNAs with defined termini that can then be joined covalently at their ends via the action of DNA ligase.

Vaccinia DNA topoisomerase, a 314-aa virus-encoded eukaryotic type I topoisomerase [11], binds to duplex DNA and cleaves the phosphodiester backbone of one strand. The enzyme exhibits a high level of sequence specificity, akin to that of a restriction endonuclease. Cleavage occurs at a consensus pentapyrimidine element 5'-(C/T)CCTT↓ in the scissile strand [12, 5, 6]. In the cleavage reaction, bond energy is conserved via the formation of a covalent adduct between the 3' phosphate of the incised strand and a tyrosyl residue (Tyr-274) of the protein [10]. Vaccinia topoisomerase can religate the covalently held strand across the same bond originally cleaved (as occurs during DNA relaxation) or it can religate to a heterologous acceptor DNA and thereby create a recombinant molecule [7, 8].

The repertoire of DNA joining reactions catalyzed by vaccinia topoisomerase has been studied using synthetic duplex DNA substrates containing a single CCCTT cleavage site. When the substrate is configured such that the scissile bond is situated near (within 10 bp of) the 3' end of a DNA duplex, cleavage is accompanied by spontaneous dissociation of the downstream portion of the cleaved strand [4]. The resulting topoisomerase-DNA complex, containing a 5' single-stranded tail, can religate to an acceptor DNA if the acceptor molecule has a 5' OH tail complementary to that of the activated donor complex. Sticky-end ligation by vaccinia topoisomerase has been demonstrated using plasmid DNA acceptors with four base overhangs created by restriction endonuclease digestion [8].

SUMMARY OF THE INVENTION

This invention provides a modified vaccinia topoisomerase enzyme containing an affinity tag which is capable of facilitating purification of protein-DNA complexes away from unbound DNA. This invention further provides a modified sequence specific topoisomerase enzyme.

This invention provides a method of ligating duplex DNAs, a method of molecular cloning of DNA, a method of synthesizing polynucleotides, and a method of gene targeting.

Lastly, this invention provides a recombinant DNA molecule composed of segments of DNA which have been joined ex vivo by the use of a sequence specific topoisomerase and which has the capacity to transform a suitable host cell comprising a DNA sequence encoding polypeptide activity.

BRIEF DESCRIPTION OF THE FIGURES

FIG. 1A: Topoisomerase-mediated cleavage of a 24-nucleotide CCCTT-containing hairpin substrate (SEQ ID NO: 6) was assayed as a function of enzyme concentration. The structure of the substrate is shown; the site of strand scission is indicated by the arrow. Reaction mixtures (20 ml) containing 50 mM Tris HCl (pH 7.5), 0.5 pmol of 5' $^{32}$P-labeled DNA, and topoisomerase were incubated at 37° C. for 5 min. Covalent complexes were trapped by addition of SDS to 1%. Samples were then electrophoresed through a 10% polyacrylamide gel containing 0.1% SDS. Covalent complex formation was revealed by transfer of radiolabeled DNA to the topoisomerase polypeptide as detected by autoradiographic exposure of the dried gel. The extent of adduct formation was quantitated by scintillation counting of an excised gel slice containing the labeled protein and was expressed as the percent of the input 5' $^{32}$P-labeled oligonucleotide that was covalently transferred to protein.

FIG. 1B: Reaction mixtures containing 50 mM Tris HCl (pH 7.5), 460 fmol of 5' $^{32}$P-labeled hairpin substrate, and 2 pmol of topoisomerase were incubated for 5 min at 37° C., then supplemented with linear pUC18 DNAceptor (350 fmol of ends) as indicated and incubated for another 5 min at room temperature. Samples were adjusted to 0.2 M NaCl and 0.5% SDS, then electrophoresed through a 1.2% agarose gel in TBE (90 mM Tris, 90 mM borate, 2.5 mM EDTA) with 0.5 mg/ml ethidium bromide. DNA was visualized by photographing the stained gel under short wave UV illumination.

FIG. 1C: The same gel was then dried and exposed for autoradiography. The positions of the radiolabeled topoisomerase-DNA "donor" complex and the pUC strand transfer product are indicated at the right. pUC18 DNA used as acceptor in the strand transfer reactions was linearized quantitatively by digestion with a single-cut restriction enzyme. The 5' phosphate termini of the linear DNAs were converted to 5' OH ends by treatment of the DNAs with calf intestinal phosphatase as indicated (CIP). The acceptor DNAs included in each reaction are specified according to lane number. Lane M (left panel) contains DNA size markers (1 HindIII digest).

FIG. 2: Monovalent, bivalent, and trivalent substrates.

Figure 1A:
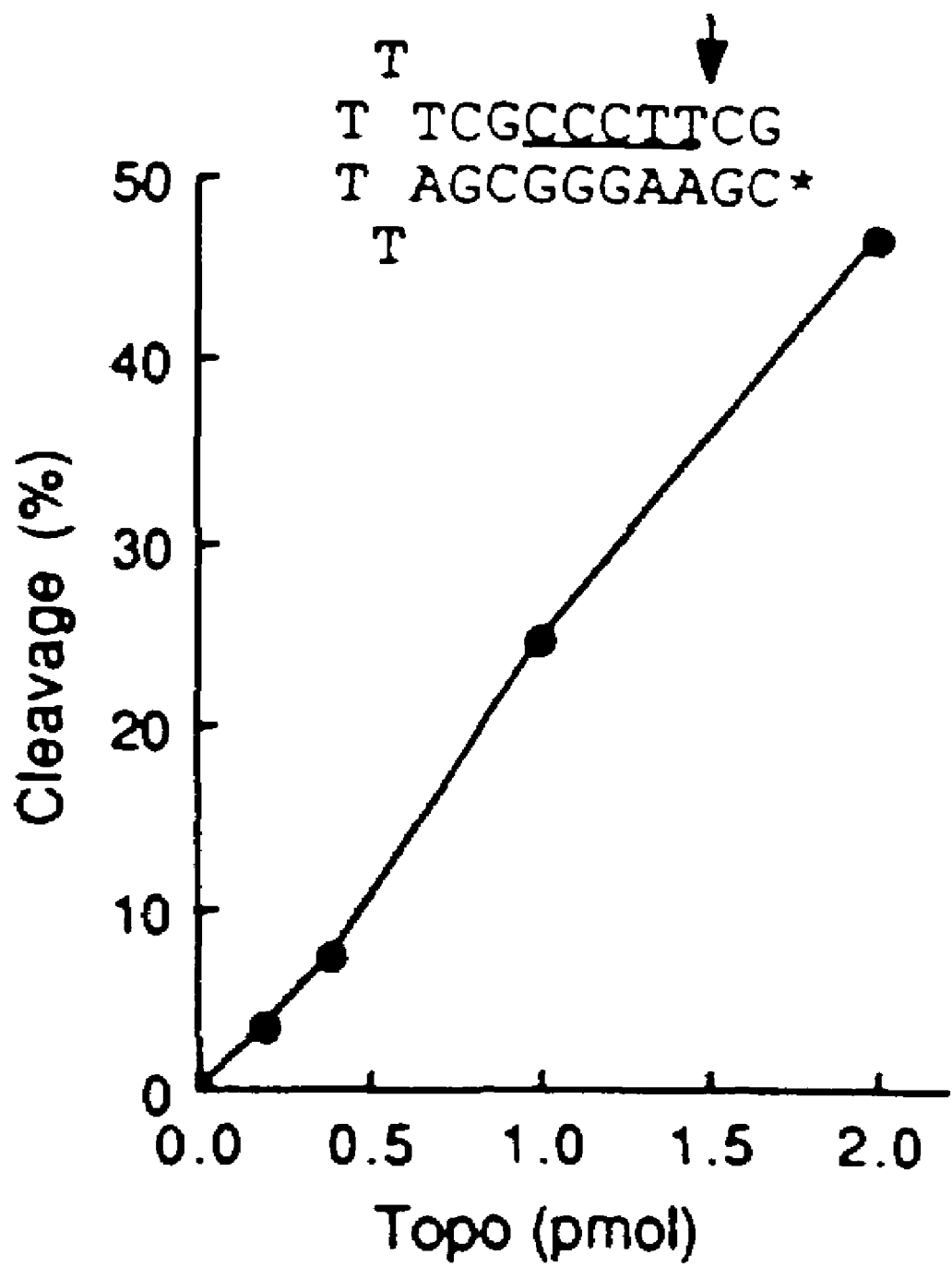
FIGS. 1A–1C: Sticky-end ligation.

The structure of the complementary hairpin oligonucoleotides S300 (SEQ ID NO: 8) and S301 (SEQ ID NO: 11) are shown. The 5' terminus is indicated by an asterisk. The CCCTT recognition site of topoisomerase cleavage is underlined. The structure of the bivalent linker DNA formed by annealing S300 and S301 strands is shown in the middle. At bottom is the structure of the trivalent Y-branched linker formed by annealing S300, S304 (SEQ ID NO: 9), and S303 (SEQ ID NO: 10) oligonucleotides.

FIGS. 3A–3C: Topoisomerase-mediated cleavage of monovalent, bivalent, and trivalent substrates.

FIG. 3A: Radiolabeled cleavage substrates were electrophoresed through a native polyacrylamide gel (7.5% acrylamide, 0.2% bisacrylamide) in TBE at 100 V. An autoradiogram of the dried gel is shown. Lane 1 contains the 5' $^{32}$P-46-mer "flip" hairpin (S300; FIG. 2). Lane 2 contains the 46-bp divalent cleavage substrate (FIG. 2). This structure was formed by annealing the 5' $^{32}$P-S300 strand to a 3-fold molar excess of unlabeled 46-nt complementary strand (S301, or "flop" strand; FIG. 2). Lane 3 contains the trivalent Y-branch substrate formed by annealing 5' $^{32}$P-S300 to two unlabeled 46-mer oligos (S303 and S304), each present at 3-fold molar excess over the labeled strand.

FIG. 3B: Cleavage reaction mixtures (20 ml) contained 50 mM Tris HCl (pH 7.5), 0.6 pmol of 5' $^{32}$P-labeled DNA, and 20 pmol of topoisomerase (lanes 2, 4, 6, and 8) were incubated at 37° C. for 5 min. Enzyme was omitted from control reactions (lanes 1, 3, 5, and 7). Covalent complexes were trapped by addition of SDS to 1%. (Note that the samples were not heat-denatured). Labeled cleavage products were resolved by SDS-PAGE. Free DNA migrated with the bromophenol blue dye front. The structures of the various covalent protein-DNA complexes are indicated at the right of the autoradiogram. The positions and sizes (in kDa) of prestained marker proteins are indicated at the left. The input substrates are illustrated at the bottom of the autoradiogram: *S300 (lanes 1 and 2); *S301 (lanes 3 and 4); *S300/S301 (lanes 5 and 6); S300/*S301 (lanes 7 and 8).

FIG. 3C: Cleavage reactions contained 0.36 pmol of radiolabeled Y-branch substrate (*S300/S303/S304) and 20 pmol of topoisomerase (lane 2). Enzyme was omitted from a control reaction (lane 1). The structures of the various covalent protein-DNA complexes are indicated at the right of the autoradiogram. The positions and sizes (in kDa) of prestained marker proteins are indicated at the left.

FIGS. 4A–4B: Topoisomerase-mediated joining of two ends via a bivalent linker.

FIG. 4A: Reaction mixtures (20 ml) contained 50 mM Tris HCl (pH 7.5), 2 pmol of topoisomerase, and either 5' $^{32}$P-labeled monovalent substrate (*S300, 0.6 pmol—lanes 1 and 2) or 5' $^{2}$P-labeled bivalent linker (0.3 pmol of *S300/S301, i.e., 0.6 pmol of ends—lanes 3 and 4). After incubation for 5 min at 37° C., the reactions were supplemented with 5'-OH HindIII-cut pUC18 DNA acceptor (380 fmol of ends) as indicated and incubated for another 5 min at room temperature. Samples were adjusted to 0.2 M NaCl and 0.5% SDS, then electrophoresed through a 1.2% agarose gel in TBE. The ethidium bromide stained gel is shown at left. The positions and sizes (kbp) of marker DNA fragments (lane M) are indicated at the left.

FIG. 4B: The same gel was dried and exposed for autoradiography. The positions of the radiolabeled topoisomerase-DNA "donor" complex and the strand transfer products are indicated at right by arrows.

FIGS. 5A–5D: Molecular cloning of DNA using vaccinia topoisomerase.

Figure 5A:
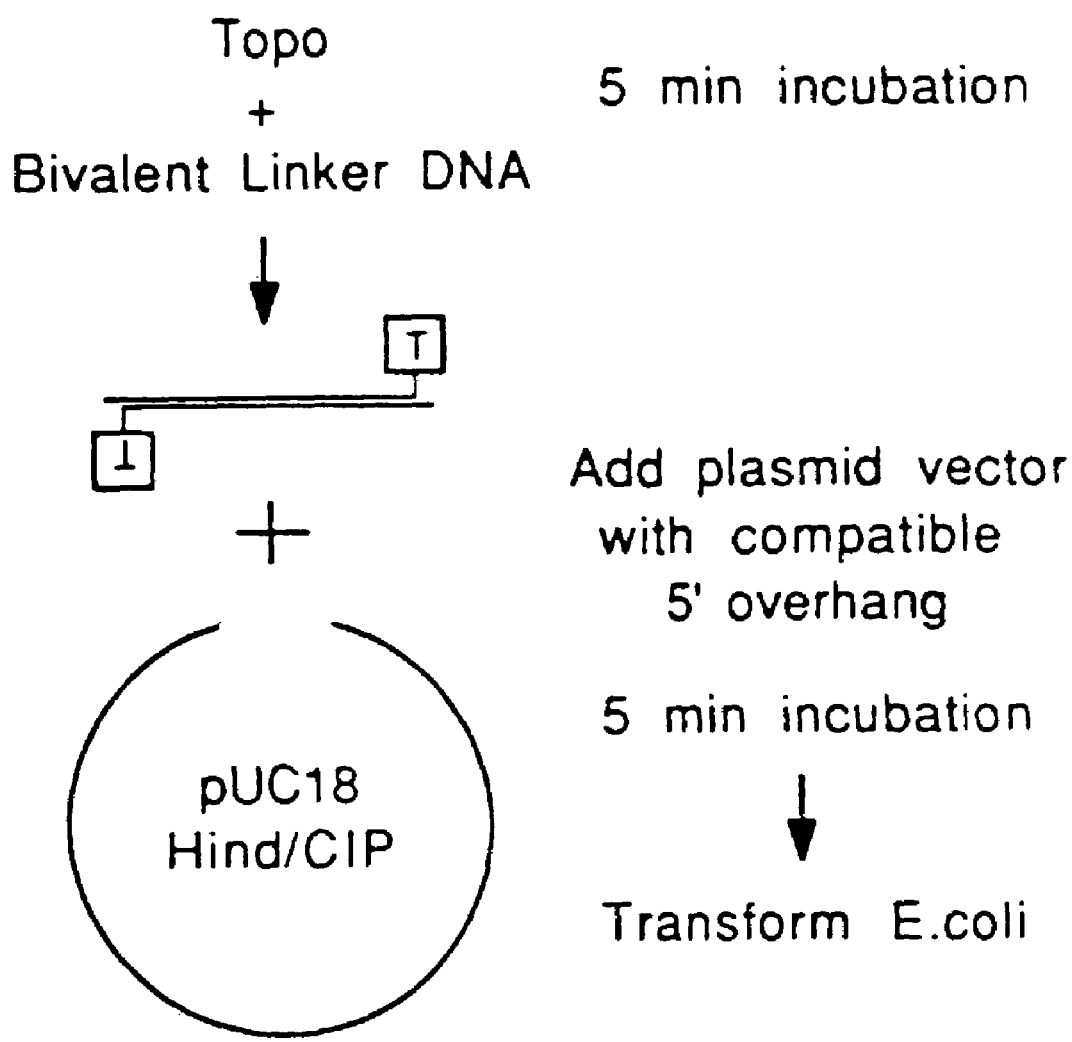

FIG. 5A: Ligation reactions for topoisomerase-based cloning were performed as described under Experimental Details. The protocol is illustrated schematically.

Figure 5B:
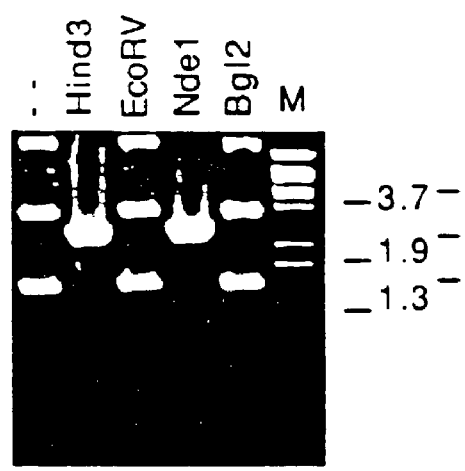
Figure 5C:
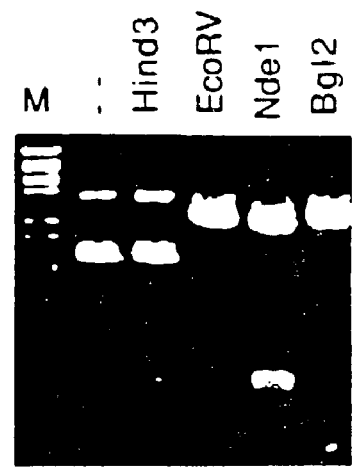

FIGS. 5B–5C: Plasmid DNA was prepared from bacteria containing pUC18 (the parent vector, FIG. 5B) and pUC-T11 (a representative tranformant from the topoisomerase ligation reaction, FIG. 5C). DNA was digested with the restriction endonucleases specified above each lane using reaction buffers provided by the vendor. Undigested plasmid DNA is shown in Lane "--". Lane M contains DNA size markers. The positions and sizes (kbp) of reference fragments are indicated. FIG. 5D: The structure of the 46-bp bivalent linker is indicated. Diagnostic restriction sites within the linker are specified above the sequence.

Figure 6A:
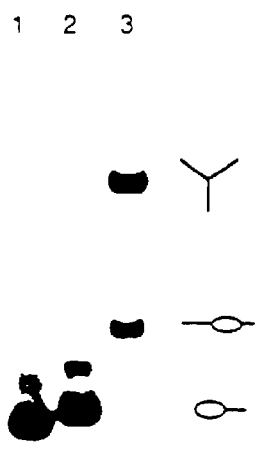
Figure 6B:
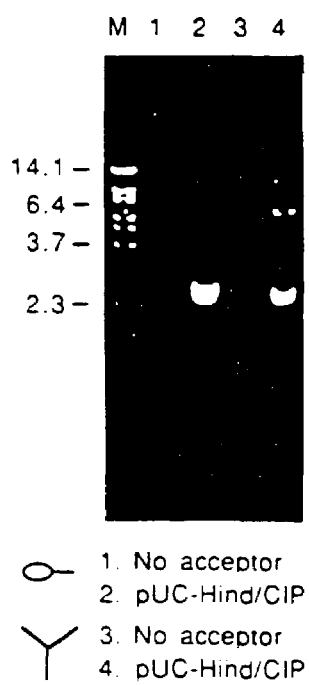

FIGS. 6A–6B: Topoisomerase-mediated joining of two ends via a trivalent linker.

FIG. 6A: Each strand of the trivalent substrate (FIG. 2) was 5' labeled and gel-purified. The Y-branched substrate was generated by annealing equimolar amounts of the three strands (*S300, *S303, *S304). The annealed product was analyzed by electrophoresis through a native 7.5% polyacrylamide gel. An autoradiograph of the gel is shown. The trivalent substrate is in lane 3. Component strands were analyzed in parallel (*S303 in lane 1; *S304 in lane 2) The structures of the labeled species are indicated at the right.

FIG. 6B: Reaction mixtures (20 ml) contained 50 mM Tris HCl (pH 7.5), 1 pmol of topoisomerase, and either 5' $^{32}$P-labeled monovalent substrate (*S304—lanes 1 and 2) or 5' $^{32}$P-labeled trivalent linker (0.3 pmol of *S300/*S303/*S304—lanes 3 and 4). Each reaction contained 350 fmol of input substrate (expressed as cleavable ends). After incubation for 5 min at 37° C., the reactions were supplemented with 5'-OH HindIII-cut pUC18 DNA acceptor (570 fmol of ends) as indicated and incubated for another 5 min at room temperature. Samples were adjusted to 0.2 M NaCl and 0.5% SDS, then electrophoresed through a 1.2% agarose gel in TBE. The ethidium bromide stained gel is shown. The positions and sizes (kbp) of marker DNA fragments (lane M) are indicated at the left.

Figure 6C:
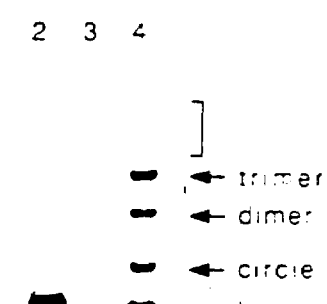

FIG. 6C: The same gel was dried and exposed for autoradiography. The positions of the radiolabeled topoisomerase-DNA "donor" complex and the strand transfer products are indicated at right by arrows and brackets.

Figure 7:
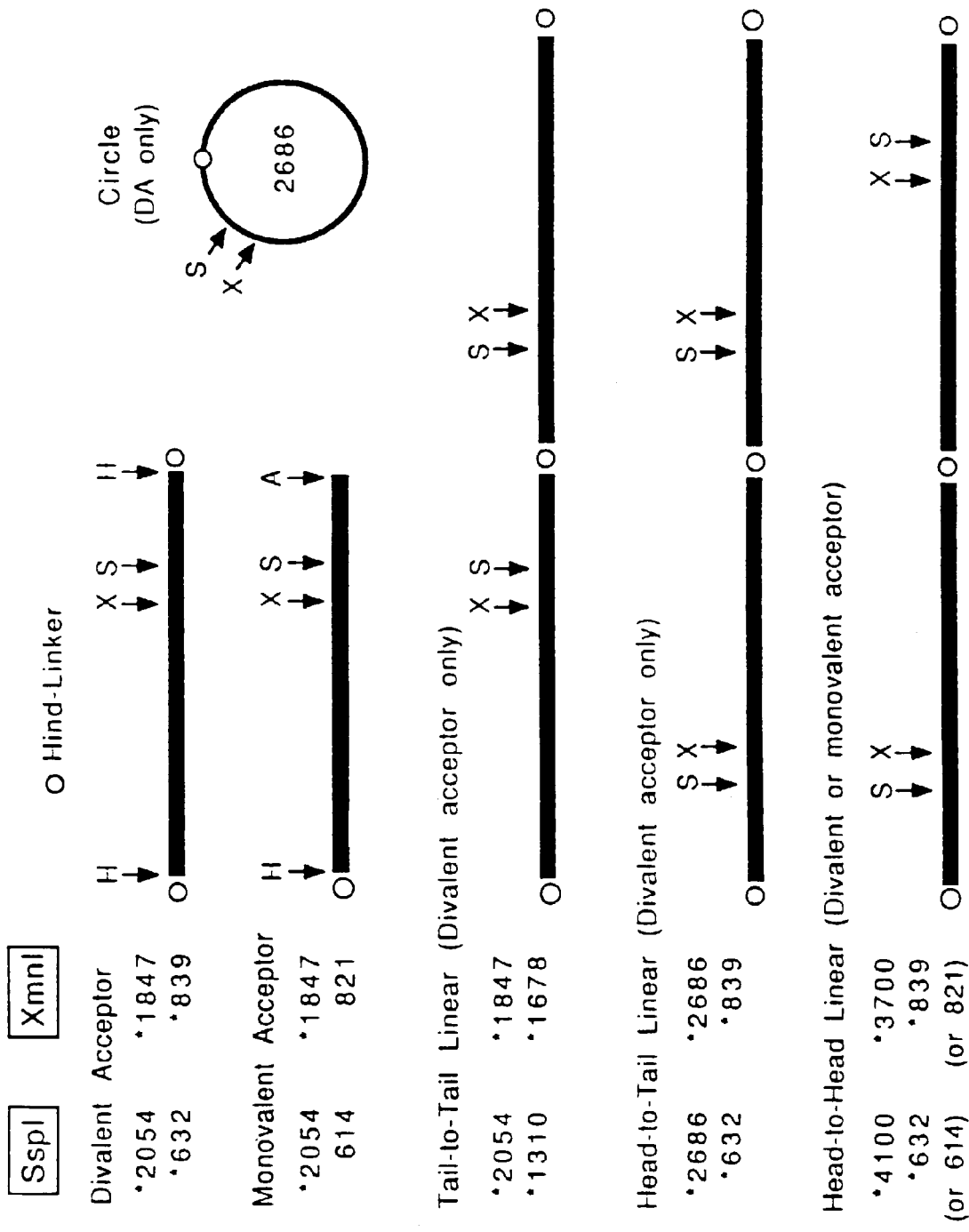

FIG. 7: Expected products of bivalent end-joining.

The locations of restriction sites for HindIII (H), XmnI (X), SspI (S), and AccI (A) within the linear pUC acceptors and anticipated ligation products are indicated by arrows. The pUC DNA is denoted by a solid bar. The predicted sizes of SspI and XmnI restriction fragments derived from each species are listed at the left. Fragments that are expected to contain radiolabeled linker DNA are indicated by asterisks.

Figure 8:
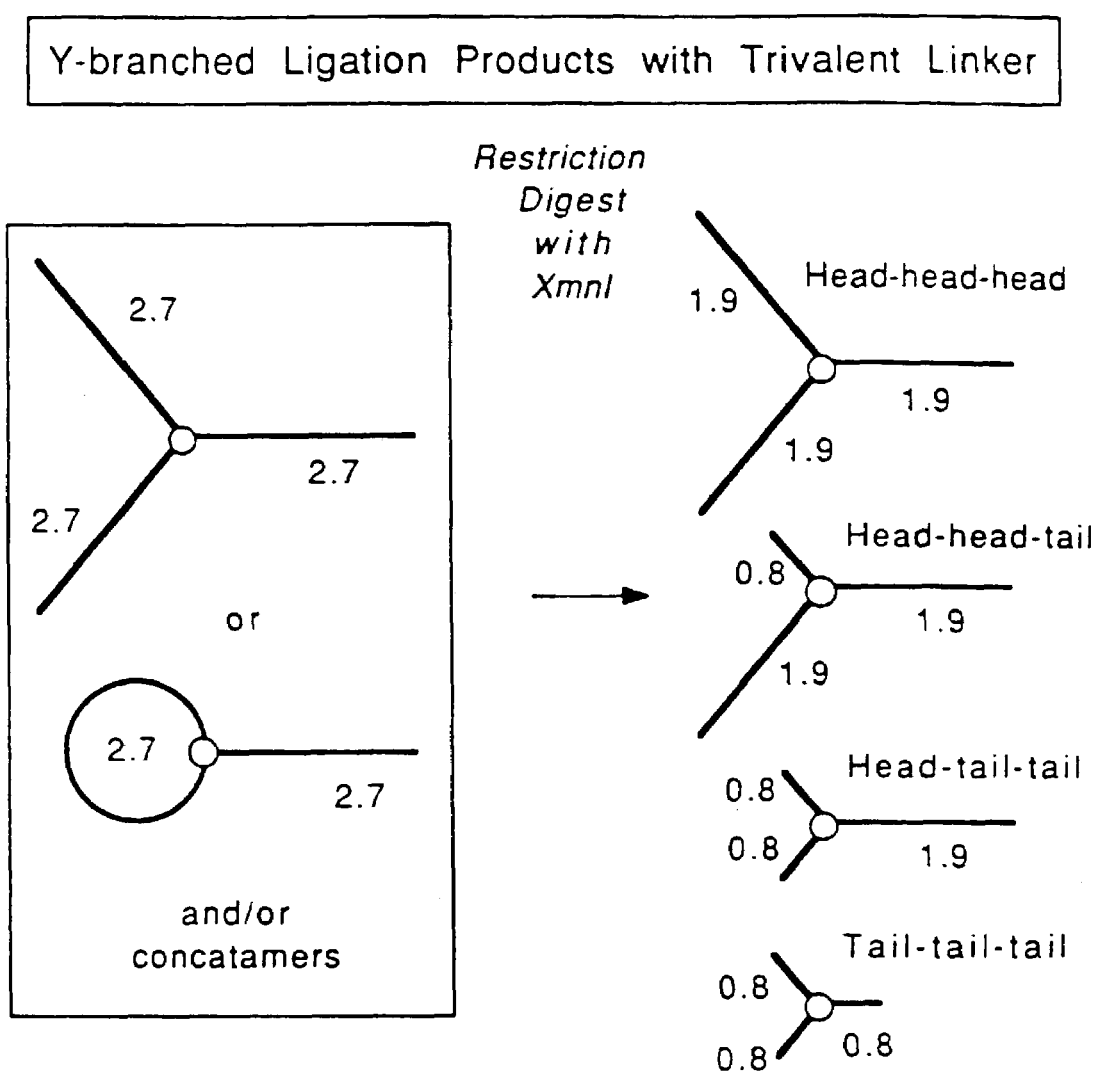

FIG. 8: Expected products of trivalent end-joining.

The expected products of trivalent end joining to pUC DNA are shown in the box. Digestion with XmnI is predicted to yield four trivalent products, which are depicted at the right. The lengths of the pUC "arms" (in kpb) are indicated.

FIGS. 9A–9C: Restriction endonuclease digestion of end-joining reaction products.

FIG. 9A: Reaction mixtures (20 ml) contained 50 Mm Tris Hcl (pH 7.5), 1 pmol of topoisomerase, and either monovalent substrate (*S300—lanes 1 and 2), divalent linker (*S300/*301—lanes 3 an 4), or trivalent linker (*S300/*S303/*S304—lanes 5 and 6). After incubation for 5 min at 37° C., the reactions were supplemented with either 5'-OH HindIII-cut pUC19 "bivalent" DNA acceptor (600 fmol linear DNA—lanes 1, 3, and 5) or 5'-OH HindIII/5'-P AccI-cut PUC19 "monovalent" acceptor (500 fmol of linear DNA—lanes 2, 4, and 6) and incubated for another 5 min at room temperature. The mixtures were adjusted to recommended restriction conditions by addition of 10× buffer concentrate (NEB2) and the samples were digested with SspI (10 units; New England BioLabs) for 60 min at 37° C. Samples were adjusted to 0.5% SDS and electrophoresed through a 1.2% agarose gel in TBE. An ethidium bromide stained gel is shown. The positions and sizes (kbp) of marker DNA fragments (lane M) are indicated at the left.

FIGS. 9B–9C: Cleavage reactions containing radiolabeled bivalent linker (lanes 1 and 2) or trivalent linker (lanes 3–5) were supplemented with divalent pUC19 acceptor (lanes 1 and 3) or monovalent pUC19 acceptor (lanes 2 and 4). A control reaction received no acceptor (lane 5). The strand transfer reaction products were digested with XmnI (40 units) for 2 h at 37° C., then analyzed by agarose gel electrophoresis. The ethidium bromide stained gel is shown (FIG. 9B). The positions and sizes (kbp) of marker DNA fragments (lane M) are indicated at the left of the photograph. The same gel was dried and exposed for autoradiography (FIG. 9C). The positions of the radiolabeled topoisomerase-DNA "donor" complex and the strand transfer products are indicated at right by arrows and brackets.

DETAILED DESCRIPTION OF THE INVENTION

This invention provides a modified vaccinia. topoisomerase enzyme containing an affinity tag. The modified vaccinia topoisomerase enzyme is capable of facilitating purification of a vaccinia topoisomerase-DNA complex from unbound DNA. This invention also provides a modified sequence specific topoisomerase enzyme. The sequence specific topoisomerase enzyme can be any site specific type I topoisomerase.

Topoisomerases are a class of enzymes that modify the topological state of DNA via the breakage and rejoining of DNA strands. Vaccinia topoisomerase enzyme is a vaccinia virus-encoded eukaryotic type I topoisomerase. In one embodiment vaccinia topoisomerase enzyme is a 314 aa virus encoded type I topoisomerase.

In another embodiment the modified vaccinia enzyme is a site-specific type I topoisomerase. Site-specific type I topoisomerases include, but are not limited to, viral topoisomerases such as pox virus topoisomerases. Examples of pox virus topoisomerases include shope fibroma virus and ORF virus. Other site specific topoisomerases are known to those skilled in the art.

In another embodiment the affinity tag includes, but is not limited to, the following: a glutathione-S-transferase fusion tag, a maltose binding protein tag, a histidine or polyhistidine tag.

In one embodiment the vaccinia topoisomerase-DNA complex is purified from unbound DNA by binding the histidine tagged topoisomerase-DNA complex to a nickel column and eluting the substrate with Imidazole.

This invention provides a duplex DNA molecule, that is, a double-stranded DNA molecule, having at each end thereof the modified vaccinia topoisomerase enzyme.

Vaccinia topoisomerase binds to duplex DNA and cleaves the phosphodiester backbone of one strand while exhibiting a high level of sequence specificity, cleaving at a consensus pentapyrimidine element 5'-(C/T)CCTT↓, or related sequences, in the scissile strand. In one embodiment the scissile bond is situated in the range of 2–12 bp from the 3' end of a duplex DNA. In another embodiment cleavable complex formation by vaccinia topoisomerase requires six duplex nucleotides upstream and two nucleotides downstream of the cleave site. Examples of vaccinia topoisomerase cleavable sequences include, but are not limited to, +6/−6 duplex GCCCTTATTCC (SEQ ID NO: 1), +8/−4 duplex TCGCCCTTATTC (SEQ ID NO: 2), +10/−2 duplex TGTCGCCCTTAT (SEQ ID NO: 3), and +10/−2 duplex GTGTCGCCCTTA (SEQ ID NO: 4).

As used herein, the term donor signifies a duplex DNA which contains a CCCTT cleavage site within 10 bp of the 3' end and the term acceptor signifies a duplex DNA which contains a 5'-OH terminus. Once covalently activated by topoisomerase the donor will only be transferred to those acceptor ends to which it can base pair.

This invention provides a method of ligating duplex DNAs employing the modified tagged vaccinia topoisomerase. In this method of ligation the donor duplex DNA substrate is a bivalent donor duplex DNA substrate, that is, it contains two topoisomerase cleavage sites. One embodiment comprises cleaving a donor duplex DNA substrate containing sequence specific topoisomerase cleavage sites by incubating the donor duplex DNA substrate with a sequence specific topoisomerase to form a topoisomerase-bound donor duplex DNA strand and incubating the topoisomerase-bound donor duplex DNA strand with a 5' hydroxyl-terminated compatible acceptor DNA, resulting in the ligation of the topoisomerase-bound donor duplex DNA strand to the DNA acceptor strand.

Methods of cleaving DNA by incubation with enzymes and methods of ligating DNA by incubation are known to those skilled in the art. In one embodiment the sequence specific topoisomerase is a vaccinia topoisomerase enzyme. In another embodiment the sequence specific topoisomerase is a modified vaccinia topoisomerase enzyme. In embodiments using vaccinia or modified vaccinia topoisomerase enzyme the cleavage site is an oligopyrimidine motif 5' (C/T)CCTT↓.

In one embodiment the desired subpopulation of DNA ligation product is purified by introducing to the 5' end of the donor duplex DNA an affinity label. In a preferred embodiment the affinity label is a biotin moiety and purification is performed by binding the biotin-ligated product to streptavidin. Other purification methods are known to those skilled in the art.

Bivalent end-joining allows the assembly of linear concatamers from polynucleotides with compatible ends. When the linker is designed to generate the same overhang at each cleavage site, the strand transfer products are randomly oriented as head-to-head, head-to tail, and tail-to-tail isomers. Control of the reaction can be easily achieved by using a bivalent linker containing different overhangs at each cleavage site; in this way, DNA acceptors prepared with two different restriction enzymes can be assembled in a strictly head-to-tail fashion. The ligation can be made exclusively head-to-head by combining a symmetric bivalent linker with an acceptor DNA containing asymmetric ends.

Bivalent strand transfer also results in circularization of the acceptor, a property that can be exploited for molecular cloning. For example, by placing the topoisomerase cleavage sites on the insert (a synthetic bivalent substrate) and cloning the cleaved DNA into a plasmid vector. This strategy is well-suited to the cloning of DNA fragments amplified by PCR. To clone PCR products using vaccinia topoisomerase, it is necessary to include a 10-nucleotide sequence -5'-XXXXAAGGGC- (SEQ ID NO: 5) at the 5' end of the two primers used for amplification. The 5'-XXXX segment can correspond to any 4-base overhang that is compatible with the restriction site into which the PCT product will ultimately be cloned. The amplification procedure will generate duplex molecules containing the sequence -GCCCTTxxxx-3' (SEQ ID NO: 12) at both 3' ends (where xxxx is the complement of XXXX). Incubation of the PCR product with topoisomerase will result in cleavage at both termini and allow the covalently activated PCR fragment to be ligated to vector DNA, essentially as described in FIG. 5A.

This invention also provides a method of molecular cloning of DNA. One embodiment comprises introducing to a donor duplex DNA substrate a sequence specific topoisomerase cleavage site by PCR amplifying the donor duplex DNA molecule with oligonucleotide primers containing the sequence specific topoisomerase cleavage site; incubating the donor duplex DNA with a sequence specific topoisomerase, resulting in the formation of a sequence specific topoisomerase-donor duplex DNA complex; incubating the sequence specific topoisomerase-donor duplex DNA complex with a plasmid vector with a 5' overhang compatible to the donor; incubating the sequence specific topoisomerase-donor duplex DNA complex with the plasmid vector; and transforming the plasmid vector that has been incubated into a host cell.

In one embodiment the sequence specific topoisomerase is a vaccinia topoisomerase enzyme. In another embodiment the sequence specific topoisomerase is a modified vaccinia topoisomerase enzyme. In embodiments using vaccinia or modified vaccinia topoisomerase enzyme the cleavage site is an oligopyrimidine motif 5' (C/T)CCTT↓.

PCR amplification methods are known to those skilled in the art. In one embodiment, the cloning of PCR products using vaccinia topoisomerase requires including a 10-nucleotide sequence 5'-XXXXAAGGGC- (SEQ ID NO: 5) at the 5' end of the two primers used for amplification. The 5'-XXXX segment can correspond to any 4-base overhang compatible with the restriction site into which the PCR product will be cloned. The amplification procedure will generate duplex molecules containing the sequence -GC-CCTTxxxx-3' (SEQ ID NO: 12) at both 3' ends (where xxxx is the complement of XXXX). Incubation of the PCR product with topoisomerase results in cleavage at both termini and allows the covalently activated PCR fragment to be ligated to vector DNA.

Regulatory elements required for expression include promoter or enhancer sequences to bind RNA polymerase and transcription initiation sequences for ribosome binding. For example, a bacterial expression vector includes, but is not limited to, a promoter such as the lac promoter and for transcription initiation the Shine-Dalgarno sequence and the start codon AUG. Similarly, a eukaryotic expression vector includes, but is not limited to, a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

In this invention transformation of the plasmid vector is into a prokaryotic host cell, such as a bacteria cell. In a preferred embodiment the host cell is *E. coli*.

Topoisomerase-based cloning has several advantages over conventional ligase-based cloning of PCR products. First, the topoisomerase procedure circumvents any problems associated with addition of nontemplated nucleotides by DNA polymerase at the 3' end of the amplified DNA. Any nontemplated base (N) at the 3' end of a PCR product destined for topoisomerase-based cloning (GCCCT-T°xxxxN-3') will dissociate spontaneously upon covalent adduct formation, and will therefore have no impact on the ligation to vector. Second, in topoisomerase-mediated cloning, the only molecule that can possibly be ligated is the covalently activated insert and the insert can only be transferred to the vector. There is no potential for in vitro covalent closure of the vector itself, which ensures low background. There is also no opportunity for the inserts to ligate to each other (this can be guaranteed by using 5'-phosphate-terminated PCR primers), which precludes cloning of concatameric repeats. Third, there is no need to consider the sequence of the DNA being amplified in designing the PCR primers. It is commonplace in standard cloning to introduce a restriction site into the PCR primer and to cleave the PCR products with that restriction enzyme to facilitate joining by ligase to vector. In cases where the sequence between the primers is not already known, it becomes problematic to choose a site for the primer that is not present in the amplified segment. This issue becomes even more relevant as PCR methodology advances and very long targets (10–40 kbp) are amplified routinely. The issue of internal topoisomerase cleavage sites (CCCTT or related pentapyrimidine elements) is not a significant impediment to topoisomerase-based cloning. This is because the cleavage-religation equilibrium at internal sites strongly favors the noncovalently bound state, and at those sites that are incised, only one strand of the duplex is nicked. Internal cleavage sites can be induced to religate by raising the salt concentration, which serves to dissociate noncovalently bound topoisomerase and drive the reaction equilibrium to the left. In contrast, cleavage at sites near the 3' end is virtually quantitative and is essentially irreversible until an acceptor DNA is provided.

Topoisomerase-based cloning strategies need not be limited to covalent activation of the insert. By designing a plasmid polylinker such that CCCTT sites are situated in inverted orientation on either side of a restriction site, one can generate a linear vector with topoisomerase sites at both 3' ends. Once covalently activated by topoisomerase, the vector "donor" can be used to clone any complementary insert "acceptor" (which must have 5'-OH termini), thereby precluding religation of the vector without the insert. It is worth noting that the donor complex formed upon cleavage by topoisomerase at a 3' proximal site is extremely stable. The donor molecule can be transferred nearly quantitatively to a complementary acceptor even after many hours of incubation of the covalent topo-DNA complex at room temperature. Indeed, the topo-linker complex can be denatured with 6 M guanidine HCl and then renatured spontaneously upon removal of guanidine with complete recovery of strand transferase activity. Thus, a topoisomerase-activated vector can be prepared once in quantity and used as many times as needed for molecular cloning.

This invention provides a method of synthesizing polynucleotides. One embodiment comprises annealing a multiple number of duplex DNA strands to form a branched substrate containing a sequence specific topoisomerase cleavage site at each 3' end; cleaving the branched substrate by incubation with a sequence specific topoisomerase to form a branched topoisomerase complex; and incubating the branched topoisomerase complex with complementary monovalent and/or bivalent DNA acceptors. This method of polynucleotide synthesis is useful for in vitro end-labelling, ligand tagging, molecular cloning.

In one embodiment the sequence specific topoisomerase is a vaccinia topoisomerase enzyme. In another embodiment the sequence specific topoisomerase is a modified vaccinia topoisomerase enzyme. In embodiments using vaccinia or modified vaccinia topoisomerase enzyme the cleavage site is an oligopyrimidine motif 5' (C/T)CCTT↓.

In one embodiment annealing of the duplex DNA strands is performed by mixing the DNA strands and heating to 65° C. for 5 minutes, and then allowing the mixture to slow cool to room temperature. One skilled in the art knows the procedures to follow for annealing duplex DNA.

In one embodiment three duplex DNA strands are used which form a trivalent Y-branched structure. Production of a Y-branched nucleic acid by the strand transfer reaction containing the trivalent linker can be demonstrated by diagnostic restriction digestion of the reaction products. The yield of Y-branched products can be optimized by eliminating residual bivalent and monovalent linkers from the substrate preparation or by ensuring that all trivalent linkers were saturated with three bound topoisomerase molecules. Both conditions can be met, by gel-purifying the linker and by purifying the tri-covalently activated species by sedimentation. As with bivalent ligation, the orientation of the Y-branched products can be controlled by manipulating the design of the linker, or by using asymmetric acceptors. Any head-to-head-to-head type Y-branched product of trivalent strand transfer can, in theory, be organized into a trivalent lattice by adding a second trivalent donor complex that is complementary to the "tail" of the original acceptor DNA. Donor substrates of higher order valence can be used to achieve topo-based synthesis of three dimensional lattices and polyhedra from DNA. Topoisomerase-based synthesis offers a potentially powerful alternative strategy for building complex biopolymers.

In one embodiment a duplex DNA strand is 5' labeled and the 5' labeled duplex DNA strand is annealed to the two duplex DNA strands to enable radiochemical purification of the substrate. Methods of radiochemical purification are known to those skilled in the art.

This invention provides a method of gene targeting. Gene targeting involves the introduction of DNA into a cell. The DNA is taken up into the chromosomal DNA by virtue of a topoisomerase-bound donor duplex DNA. The bound topoisomerase seals the donor DNA to chromosomal DNA. One embodiment comprises cleaving a bivalent donor duplex DNA substrate containing a sequence specific topoisomerase cleavage site by incubating the donor duplex DNA substrate with a sequence specific topoisomerase to form a topoisomerase-bound donor duplex DNA strand; and transfecting the topoisomerase-bound donor duplex DNA to a suitable cell.

In one embodiment the sequence specific topoisomerase is a vaccinia topoisomerase enzyme. In another embodiment the sequence specific topoisomerase is a modified vaccinia topoisomerase enzyme. In embodiments using vaccinia or modified vaccinia topoisomerase enzyme the cleavage site is an oligopyrimidine motif 5' (C/T)CCTT↓.

Transfection may be performed by any of the standard methods known to one skilled in the art, including, but not limited to electroporation, calcium phosphate transfection or lipofection.

This invention provides a recombinant DNA molecule composed of segments of DNA which have been joined ex vivo or in vitro by the use of a sequence specific topoisomerase and which has the capacity to transform a suitable host cell comprising a DNA sequence encoding polypeptide activity.

In one embodiment the sequence specific topoisomerase is a vaccinia topoisomerase enzyme. In another embodiment the sequence specific topoisomerase is a modified vaccinia topoisomerase enzyme. In embodiments using vaccinia or modified vaccinia topoisomerase enzyme the cleavage site is an oligopyrimidine motif 5' (C/T)CCTT↓.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

I. Methods

A) Enzyme Purification:

Vaccinia DNA topoisomerase was expressed in *Escherichia coli* and purified as described [9]. The heparin agarose enzyme fraction used in the present study was the same preparation described previously [9]. The enzyme was nearly homogeneous with respect to the 33 kDa topoisomerase polypeptide, as determined by SDS-polyacrylamide gel electrophoresis. Protein concentration was determined using the Biorad dye reagent, taking bovine serum albumin as the standard.

B) Synthesis of 5' Labeled Oligonucleotide Substrates:

Synthesis of DNA oligonucleotides via DMT-cyanoethyl phosphoramidite chemistry was performed by the Sloan-Kettering Microchemistry Laboratory using an Applied Biosystems model 380B or model 394 automated DNA synthesizer according to protocols specified by the manufacturer. Oligonucleotides containing the CCCTT cleavage motif were labeled at the 5' end via enzymatic phosphorylation in the presence of [g$^{32}$P]ATP and T4 polynucleotide kinase. Reaction mixtures (25 ml) typically contained 50 mM Tris HCl (pH 8.0), 10 mM dithiothreitol, 10 mM MgCl$_2$, 0.1 mM ATP, 100 mCi [g$^{32}$P]ATP, T4 polynucleotide kinase (20 units, Bethesda Research Laboratories), and 500 pmol of DNA oligonucleotide (DNA was quantitated by A$_{260}$). Incubation was for 60 min at 37° C. Labeled DNA was freed of protein and radioactive nucleotide by electrophoresis through a non-denaturing 18%. polyacrylamide gel. Full-sized labeled oligonucleotide was localized by autoradiographic exposure of the wet gel and the labeled DNA was recovered from an excised gel slice by soaking the slice in 0.4 ml H$_2$O for 8 h at room temperature. Hybridization of labeled DNAs to complementary oligonucleotides was performed in 0.2 M NaCl by heating to 75° C. followed by slow cooling to room temperature. Annealed substrates were stored at 4° C.

C) Topoisomerase-based Cloning:

Reaction mixtures containing 50 mM Tris HCl (pH 7.5), 2 pmol of topoisomerase, and either monovalent linker (0.6 pmol) or bivalent linker (0.3 pmol) were incubated for 5 min at 37° C. A control reaction contained topoisomerase but no DNA substrate. Each mixture was then supplemented with 5'-OH HindIII-cut pUC18 DNA acceptor (380 fmol of ends) and incubated for another 5 min at room temperature. An aliquot (1 ml) of each sample was used to transform *E. coli* DH5a using a BioRad Gene Pulser electroporation apparatus. Preparation of bacterial cells and electrotransformation were carried out as prescribed by the manufacturer. Aliquots of transformed bacteria were plated on LB agar containing 0.1 mg/ml ampicillin.

II. Example 1

Sticky End Ligation

Figures 1B, 1C:
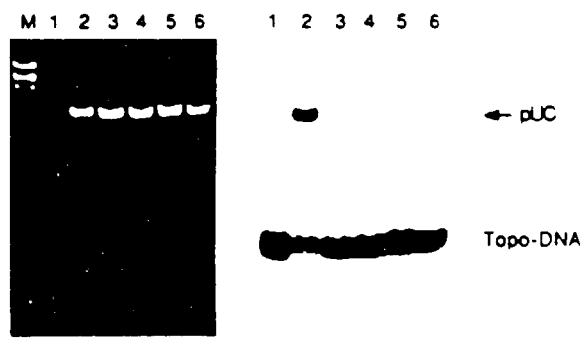

The vaccinia topoisomerase was capable of sticky-end ligation of duplex DNAs containing only 2 bases of potential complementarity, as shown in FIG. 1. In this experiment, the "donor" was a 24-mer hairpin oligonucleotide containing a single CCCTT motif (a "monovalent" substrate) with the scissile bond located 2 bases from the 3' blunt end (FIG. 1A). The extent of cleavage of this substrate was proportional to enzyme concentration (FIG. 1A). The topoisomerase-DNA complex migrated as a discrete species during native agarose gel electrophoresis (FIG. 1C). Addition of unlabeled 5' hydroxyl-terminated CpG tailed linear pUC18 DNA (generated by digestion of pUC DNA with AccI followed by treatment with alkaline phosphatase) resulted in transfer of the topoisomerase-bound DNA strand to the linear DNA "acceptor." The product of the strand transfer reaction was a radiolabeled 2.7 kbp linear form containing a hairpin end (FIG. 1C, lane 2). AccI-restricted plasmid DNA containing a 5'-phosphate terminus was inert as an acceptor (FIG. 1C, lane 3). [The requirement for a 5'OH-terminated acceptor excluded the possibility that the reaction products might be formed by a conventional DNA ligase contaminating the topoisomerase preparation]. Linear plasmid DNA containing non-complementary 5'-OH overhangs generated by restriction with EcoRI (5'-AATT) or HindIII (5'-AGCT) were ineffective as acceptors (FIG. 1C, lanes 4 and 6), as was 5'-OH blunt-ended linear DNA generated by restriction with SmaI (lane 5).

III. Example 2

Divalent Linkers as Donors

Two 46-mer DNA strands were annealed to form a "divalent" 46-bp substrate containing a topoisomerase cleavage site 4 nucleotides from each 3' end (FIG. 2). Successful annealing of the constituent strands was evinced by the reduced mobility of the duplex molecule during native gel electrophoresis (FIG. 3A, lane 2) compared to that of the hairpin DNA (FIG. 3A, lane 1). Either the "flip" or "flop" monovalent hairpins were readily cleaved by vaccinia topoisomerase, resulting in the formation of a covalent protein-DNA adduct which migrated at 43 kDa during SDS-PAGE (FIG. 3B, lanes 2 and 4). Incubation of topoisomerase with the divalent duplex substrate yielded two complexes of 46 kDa and 72 kDa; the 46 kDa species represents a single molecule of topoisomerase bound covalently at one of the CCCTT cleavage sites; the 72 kDa complex arises by cleavage at both sites on the same DNA molecule (FIG. 3B, lanes 6 and 8).

The monovalent hairpin DNA was transferred virtually quantitatively to linear pUC DNA containing a complementary 5'-OH-AGCT overhang (FIGS. 4A–4B, lane 2). Incubation of the bivalent topoisomerase-DNA complex with the same acceptor yielded a complex set of products arising from ligation of the bivalent linker to two complementary ends of the linear pUC acceptor (FIGS. 4A–4B, lane 4). These included circular pUC and linear pUC concatamers. A significant fraction of the pUC acceptor molecules were subject to bivalent end-joining, as reflected in the distribution of EtBr-stained DNA products (FIG. 4A, lane 4). All ligation events were via the radiolabeled linker DNA, which became incorporated into the reaction products (FIG. 4B, lane 4).

IV. Example 3

Molecular Cloning of DNA Using Vaccinia Topoisomerase

The ability of topoisomerase to join both ends of a linear DNA to a complementary acceptor suggested an alternative approach to molecular cloning. In the scheme shown in FIG. 5, the "insert" was a bivalent 46-bp linker containing CCCTT sites at both 3' ends. The sequence of the linker included restriction sites for endonucleases NdeI, BglII, and EcoRV. Cleavage of the bivalent linker by topoisomerase generated a 4-base overhang complementary to a HindIII restriction site. The "vector" was pUC DNA that had been cleaved with HindIII and dephosphorylated with alkaline phosphatase.

Addition of the vector to the bivalent topoisomerase-DNA donor complex should result in covalent joining of the insert to the vector. Upon transformation into E. coli, those molecules that had been circularized should be able to give rise to ampicillin-resistant colonies. It was found that the yield of ampicillin-resistant colonies from bacteria transformed with a topoisomerase reaction mixture containing linear pUC and the bivalent linker was 110-fold higher than that observed for bacteria transformed with control topoisomerase reactions containing linear pUC and either monovalent linker or no linker.

Plasmid DNA was recovered from cultures of six individual transformants and analyzed by restriction endonuclease digestion in parallel with pUC18 plasmid DNA (FIG. 5B). [The restriction pattern for the recombinant clone pUC-T11 shown in FIG. 5C was indistinguishable from that of the five other clones, which are not shown]. Whereas the starting pUC18 plasmid contains no sites for EcoRV and BglII, the recombinant clone contains a single site for each enzyme, attributable to the insertion of the bivalent linker, which contains these restriction sites. Similarly, the starting plasmid contains a single NdeI site, whereas the recombinant clone contains a second NdeI site in the linker insert. The size of the novel NdeI fragment in pUC-T11 indicated that the linker DNA was inserted within the pUC polylinker as expected. This was confirmed by the finding that the recombinant plasmid had lost the original HindIII site upon strand transfer by topoisomerase to the HindIII overhang (the strand transfer reaction should generate the sequences AAGCTA and TAGCTT at the plasmid-insert junctions, which would not be cut by HindIII). The restriction site for SphI, which is located immediately next to the HindIII site in the polylinker, was retained in all recombinant clones (not shown), indicating that loss of the HindIII site was not caused by deletions occurring during strand transfer. Thus, the bivalent linker DNA was successfully cloned into the pUC18 vector in a simple procedure that—exclusive of the bacterial transformation step—takes only 10 minutes to execute.

V. Example 4

Trivalent Linkers as Donors

Three 46-mer DNA strands were annealed to form a "trivalent" Y-branched substrate containing a topoisomerase cleavage site 4 nucleotides from each 3' end (FIG. 2). To optimize radiochemical purity of the substrate, one of the strands was 5' radiolabeled and annealed to the two other strands, which were present in molar excess (FIG. 3A). The radiolabeled Y-branched substrate migrated more slowly than a 46-bp linear duplex molecule during native gel electrophoresis (FIG. 3A, lane 3). Anomalous electrophoretic behavior of the Y molecule was also evident during SDS-PAGE, where the trivalent substrate migrated at a position equivalent to a 39 kDa protein (FIG. 3C, lane 1). The Y-branch structure was cleaved quantitatively upon incubation with topoisomerase; three complexes were resolved, corresponding to Y-molecules with one, two, or three covalent bound topo polypeptides (FIG. 3C). Most of the cleaved DNAs contained two or three bound topoisomerase molecules.

To test strand transfer by the trivalent donor complex, the Y-branched molecule was prepared by annealing equimolar amounts of the constituent strands, each of which was radiolabeled. Although the three-strand Y-form constituted the predominant product of the annealing reaction (FIG. 6A, lane 3), bivalent linkers were present as well (these molecules contain an unpaired "bubble" as indicated in FIG. 6). The radiolabeled substrate was transferred quantitatively from the topoisomerase-DNA donor complex to a linear pUC18 acceptor containing a complementary 5'-OH-AGCT overhang (FIG. 6C, compare lanes 3 and 4). A complex array of multivalent ligation products was apparent by EtBr-staining and by autoradiography (FIGS. 6B–6C, lane 4). These included circular pUC and linear pUC concatamers as well as higher order structures (the species indicated by the bracket in FIG. 6C). None of the concatamers or higher order forms were observed in a control strand transfer reaction containing a monovalent DNA linker (FIGS. 6B–6C, lane 2).

VI. Example 5

Characterization of the Trivalent Strand Transfer Products

The recombinant molecules generated by topoisomerase-mediated end-joining were analyzed further by digestion with restriction endonucleases that cleave once within the pUC sequence. In FIG. 7, the anticipated products of bivalent end-joining by topoisomerase are shown, along with the restriction fragments expected for each product upon digestion with SspI and XmnI. The products of trivalent end-joining are illustrated in FIG. 8. Experimental results showing the spectrum of strand transfer products after digestion with SspI and XmnI are shown in FIG. 9. In this analysis, each linker, which upon cleavage generated a tailed donor complex compatible with a HindIII restriction site, was tested with two acceptor molecules, one bivalent and one monovalent. The bivalent acceptor was linear pUC19 containing 5'-OH HindIII overhangs on both ends. Strand transfer of a polyvalent linker to the bivalent acceptor allows for the formation of circular and linear concatamers in a head-to-head, tail-to-tail, or head-to tail fashion, as shown in FIG. 7. The monovalent acceptor was pUC19 containing a 5'-OH HindIII site at one end and a 5'-phosphate AccI site at the other end. Transfer of the linker by topoisomerase to the AccI terminus is precluded completely on two grounds; first, because the ends are not complementary and second, because topoisomerase cannot religate to a 5'-phosphate strand. A monovalent acceptor will react with the topoisomerase donor complex at available compatible termini, but will not be able to form circles or concatameric arrays. The structures of the various species can thus be inferred by direct comparison of the restriction digests from reaction in which monovalent, bivalent, and trivalent linkers were reacted with monovalent and bivalent acceptors.

Consider the SspI digests of topoisomerase strand transfer products in FIG. 9A. The monovalent linker was joined to either end of the bivalent pUC19 acceptor, but could not support circularization or dimerization. Hence the products were cleaved by SspI to yield two fragments derived from linear monomers (FIG. 9A, lane 1) (see FIG. 7). Ligation of the bivalent linker to bivalent acceptor yielded three additional products, a 4.1 kbp fragment diagnostic of head-to-head multimer formation, a 1.3 kbp fragment indicative of tail-to-tail ligation, and a 2.7 kbp species that derived from a circular molecule (FIG. 9A, lane 3). Ligation of the bivalent linker to a monovalent acceptor yielded the 4.1 kbp head-to-head fragment, but no fragments indicative of tail-to-tail or circular products (FIG. 9A, compare lanes 3 and 4). This was precisely as expected, because the AccI "tail" was inert for strand transfer. Reactions containing the trivalent Y-linker and bivalent acceptor yielded two novel high molecular weight products not observed for the bivalent linker (FIG. 9A, lane 5). The largest product (indicated by the arrowhead in FIG. 9A), which was also observed with trivalent linker and monovalent acceptor (FIG. 9A, lane 6), must correspond to a Y-branched recombinant containing three pUC molecules ligated in head-to head fashion. The length of each arm is predicted to be 2 kbp. The electrophoretic mobility of this species was anomalously slow, as expected for a branched DNA. The higher order complex unique to the bivalent acceptor was presumed to be a Y-branched product containing pUC19 DNA ligated in a mixed head-head and head-tail orientation.

Digestion of the strand transfer products with XmnI confirmed and extended these findings (FIGS. 9B–9C) The digest of a reaction containing labeled bivalent linker and unlabeled bivalent pUC acceptor yielded diagnostic linear fragments of 3.7 kbp (head-to-head multimer), 1.7 kbp (tail-to-tail multimer) and 2.7 kbp (circle). These products were detected by EtBr-staining and by autoradiography (FIG. 9B, lanes 1). The 1.7 kbp species indicative of tail-to-tail ligation migrated just ahead of a 1.85 fragment (derived either from end-tagged linear monomers or from head-to-tail multimers). The 1.7 kbp species was absent from the digest of products formed with the monovalent pUC acceptor (FIG. 9B, lanes 2). Similarly, the 2.7 kbp species and the radiolabeled 0.8 kbp fragment (diagnostic of ligation to the "tail" end of pUC) were absent from the monovalent acceptor digest (FIG. 9B, lane 2).

The XmnI digest of products formed with labeled trivalent linker and bivalent pUC19 acceptor contained four unique species not seen with the bivalent linker (FIG. 9B, compare lanes 3 and 1) Three of these molecules were readily apparent as high molecular weight EtBr-stained bands. The fourth species migrated barely in advance of the head-to-head linear fragment and was best appreciated in the autoradiograph (FIG. 9C, lane 3). These molecules correspond to the four possible Y-branch structures shown in FIG. 8. A priori, if there was no bias in ligation orientation, one would expect a 1:3:3:1 distribution of head-head-head, head-head-tail, head-tail-tail, and tail-tail-tail isomers. Indeed, this is what was observed experimentally (FIG. 9B, lane 3). Consistent with the predicted structures of the Y-branched products, only the largest species (head-head-head) was detected in the reaction of trivalent linker with monovalent pUC acceptor.

References:

1. Chen, J., and Seeman, N. C. (1991) *Nature* 350: 631–633.
2. Cheng, S., et al. (1994) *Proc. Natl. Acad. Sci. USA* 91: 5695–5699.
3. Clark, J. M. (1988) *Nucleic Acids Res.* 16: 9677–9686.
4. Morham, S. G., and Shuman, S. (1992) *J. Biol. Chem.* 267: 15984–15992.
5. Shuman, S. (1991a) *J. Biol. Chem.* 266: 1796–1803.
6. Shuman, S. (1991b) *J. Biol. Chem.* 266: 11372–11379.
7. Shuman, S. (1992a) *J. Biol. Chem.* 267: 8620–8627.
8. Shuman, S. (1992b) *J. Biol. Chem.* 267: 16755–16758.
9. Shuman, S., et al. (1988) *J. Biol. Chem.* 263: 16401–16407.
10. Shuman, S., et al. (1989) *Proc. Natl. Acad. Sci. USA* 86: 9793–9797.
11. Shuman, S., and Moss, B. (1987) *Proc. Natl. Acad. Sci. USA* 84: 7478–7482.
12. Shuman, S., and Prescott, J. (1990) *J. Biol. Chem.* 265: 17826–17836.
13. Stivers, J. T., et al. (1994) *Biochemistry* 33: 327–339.

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

GCCCTTATTC CC                                                              12

(2) INFORMATION FOR SEQ ID NO: 2:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

TCGCCCTTAT TC                                                              12

(2) INFORMATION FOR SEQ ID NO: 3:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

TGTCGCCCTT AT                                                              12

(2) INFORMATION FOR SEQ ID NO: 4:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

GTGTCGCCCT TA                                                                                     12

(2) INFORMATION FOR SEQ ID NO: 5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

NNNNAAGGGC                                                                                        10

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

CGAAGGGCGA TTTTTCGCCC TTCG                                                                        24

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

GCTTCCCGCT TTTAGCGGG AAGC                                                                         24

(2) INFORMATION FOR SEQ ID NO: 8:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

AGCTAAGGGC ATATGAGATC TGAATTCGAT ATCATCGCCC TTAGCT                                                46

(2) INFORMATION FOR SEQ ID NO: 9:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

TCGATTCCCG TATACTCTAG ACTTAAGCTA TAGTAGCGGG AATCGA            46

(2) INFORMATION FOR SEQ ID NO: 10:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

AGCTAAGGGC ATATGAGATC TGAATTCGAT ATCATCGCCC TTAGCT            46

(2) INFORMATION FOR SEQ ID NO: 11:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

TCGATTCCCG TATACTCTAG ACTTAAGCTA TAGTAGCGGG AATCGA            46

(2) INFORMATION FOR SEQ ID NO: 12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

GCCCTTNNNN            10

(2) INFORMATION FOR SEQ ID NO: 13:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

GCCCTTNNNN N            11

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

TTGGTACCAT GGTCGGGAAT CGA            23

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

AACCATGGTA CCAGCCCTTA GCT                    23

What is claimed is:

1. A method for ligating duplex DNAs comprising contacting a first duplex DNA with a second duplex DNA, wherein (a) the first duplex DNA has a site-specific type I topoisomerase covalently bound at each of its ends; (b) the second duplex DNA has a terminal hydroxyl at each end; and (c) the contacting is done under conditions permitting the site-specific type I topoisomerase to ligate the first duplex DNA to the second duplex DNA, thereby ligating the first and second duplex DNAs.

2. The method of claim 1, wherein the type I topoisomerase is a vaccinia topoisomerase.

3. The method of claim 2, wherein the vaccinia topoisomerase comprises an affinity tag.

4. The method of claim 3, wherein the affinity tag is histidine, polyhistidine, glutathione-S-transferase or maltose binding protein.

5. The method of claim 1, wherein the first or second duplex DNA further comprises an affinity tag.

6. The method of claim 5, wherein the affinity tag is biotin.

7. The method of claim 1, wherein the first or second duplex DNA is a plasmid vector.

8. The method of claim 1, wherein at least one end of the first duplex DNA comprises an overhang that is complementary to an overhang of the second duplex DNA.

9. The method of claim 8, wherein the overhang is 2–12 nucleotides long.

10. The method of claim 9, wherein the overhang is two nucleotide bases long.

11. The method of claim 9, wherein the overhang comprises a restriction endonuclease half-site.

12. A method for ligating duplex DNAs comprising contacting a first duplex DNA with a second duplex DNA, wherein (a) the first duplex DNA has a site-specific type I topoisomerase covalently bound at one end; (b) the second duplex DNA has a terminal hydroxyl end; (c)(i) the site-specific type I topoisomerase and/or (ii) the first and/or second duplex DNA further comprises an affinity tag; and (d) the contacting is done under conditions permitting the site-specific type I topoisomerase to ligate the first duplex DNA to the second duplex DNA, thereby ligating the first and second duplex DNAs.

13. The method of claim 12, wherein the type I topoisomerase is a vaccinia topoisomerase.

14. The method of claim 13, wherein the vaccinia topoisomerase comprises an affinity tag.

15. The method of claim 14, wherein the affinity tag is histidine, polyhistidine, glutathione-S-transferase or maltose binding protein.

16. The method of claim 12, wherein the first or second duplex DNA further comprises an affinity tag.

17. The method of claim 16, wherein the affinity tag is biotin.

18. The method of claim 12, wherein the first or second duplex DNA is a plasmid vector.

19. The method of claim 12, wherein the topoisomerase-bound end of the first duplex DNA comprises an overhang that is complementary to an overhang at the hydroxyl-terminated end of the second duplex DNA.

20. The method of claim 19, wherein the overhang is 2–12 nucleotide bases long.

21. The method of claim 20, wherein the overhang is two nucleotide bases long.

22. The method of claim 20, wherein the overhang comprises a restriction endonuclease half-site.

23. The method of claim 12, wherein the method is repeated a plurality of times so as to concatenate three or more duplex DNAs.

* * * * *

UNITED STATES PATENT AND TRADEMARK OFFICE
CERTIFICATE OF CORRECTION

| | | |
|---|---|---|
| PATENT NO. | : 7,026,141 B2 | Page 1 of 1 |
| APPLICATION NO. | : 10/360478 | |
| DATED | : April 11, 2006 | |
| INVENTOR(S) | : Stewart Shuman | |

It is certified that error appears in the above-identified patent and that said Letters Patent is hereby corrected as shown below:

In The Specification

In column 1, beginning at line 10 and ending at line 14, please delete:

"This invention was made with support under Grant No. GM-46330 from the National Institutes of Health, U.S. Department of Health and Human Services. Accordingly, the United States Government has certain rights in the invention."

and insert:

--This invention was made with government support under grant number GM046330 awarded by the National Institutes of Health. The government has certain rights in the invention.--

Signed and Sealed this
Twenty-ninth Day of March, 2016

Michelle K. Lee
*Director of the United States Patent and Trademark Office*